(12) United States Patent
Heffels et al.

(10) Patent No.: US 7,428,051 B2
(45) Date of Patent: Sep. 23, 2008

(54) DEVICE FOR THE IR-SPECTROMETRIC ANALYSIS OF A SOLID, LIQUID OR GASEOUS MEDIUM

(75) Inventors: Camiel Heffels, Ditzingen (DE); Dirk Steinmueller, Karlsruhe (DE); Dick Scholten, Stuttgart (DE); Peter Lindmueller, Essingen (DE)

(73) Assignee: Endress + Hauser Conducta Gesellschaft fur Mess-u. Regeltechnik mgH + Co. KG, Gerlingen (DE)

( * ) Notice: Subject to any disclaimer, the term of this patent is extended or adjusted under 35 U.S.C. 154(b) by 141 days.

(21) Appl. No.: 10/522,158

(22) PCT Filed: Jul. 18, 2003

(86) PCT No.: PCT/EP03/07838

§ 371 (c)(1),
(2), (4) Date: Oct. 24, 2005

(87) PCT Pub. No.: WO2004/013621

PCT Pub. Date: Feb. 12, 2004

(65) Prior Publication Data

US 2006/0115201 A1 Jun. 1, 2006

(30) Foreign Application Priority Data

Jul. 24, 2002 (DE) ................. 102 33 710
Apr. 9, 2003 (DE) ................. 103 16 514

(51) Int. Cl.
*G01N 21/31* (2006.01)
*G01J 1/44* (2006.01)
*G02B 5/28* (2006.01)
*G02B 5/04* (2006.01)
*G02B 5/12* (2006.01)
*G02B 6/34* (2006.01)
*G02B 6/42* (2006.01)

(52) U.S. Cl. ............. 356/416; 356/226; 356/235; 359/888; 359/889; 359/833; 359/834; 250/227.24; 250/227.25; 250/227.28

(58) Field of Classification Search ............ 356/51, 356/416, 226, 235; 359/833–834, 888–889; 250/227.24–227.25, 227.28
See application file for complete search history.

(56) References Cited

U.S. PATENT DOCUMENTS 5,185,834 A * 2/1993 Day et al. ............. 385/47

(Continued)

OTHER PUBLICATIONS

USPTO Translation of DE 10034220, Kupper, Anne, Jan. 31, 2002, translated Jun. 2007 by the McElroy Translation Company.*

*Primary Examiner*—Gregory J. Toatley, Jr.
*Assistant Examiner*—Bryan Giglio
(74) *Attorney, Agent, or Firm*—Bacon & Thomas, PLLC

(57) ABSTRACT

The invention relates to a device for the IR-spectrometric analysis of a solid, liquid or gaseous medium. The device includes a process probe, which has a reflection element. The device additionally includes a linear variable filter, at least one detector element, and a control/evaluation unit. At least one light source is also provided, the light of which is coupled into the reflection element via a collimating optics. At least one optical waveguide having a light input section and a light output section is provided. The light is guided via the light output section of the optical waveguide into a defined region of the linear variable filter. The detector element and the linear variable filter are arranged movably relative to one another over approximately the length of the linear variable filter. The control/evaluation unit determines the spectrum of the medium on the basis of the measured values delivered from the detector element.

18 Claims, 8 Drawing Sheets

U.S. PATENT DOCUMENTS

| | | | | |
|---|---|---|---|---|
| 5,473,162 A | * | 12/1995 | Busch et al. | 250/341.6 |
| 5,703,366 A | * | 12/1997 | Sting et al. | 250/341.2 |
| 5,754,722 A | * | 5/1998 | Melling | 385/115 |
| 5,815,278 A | * | 9/1998 | Johnston et al. | 356/445 |
| 5,828,452 A | * | 10/1998 | Gillispie et al. | 356/328 |
| 2002/0158211 A1 | * | 10/2002 | Gillispie | 250/458.1 |

* cited by examiner

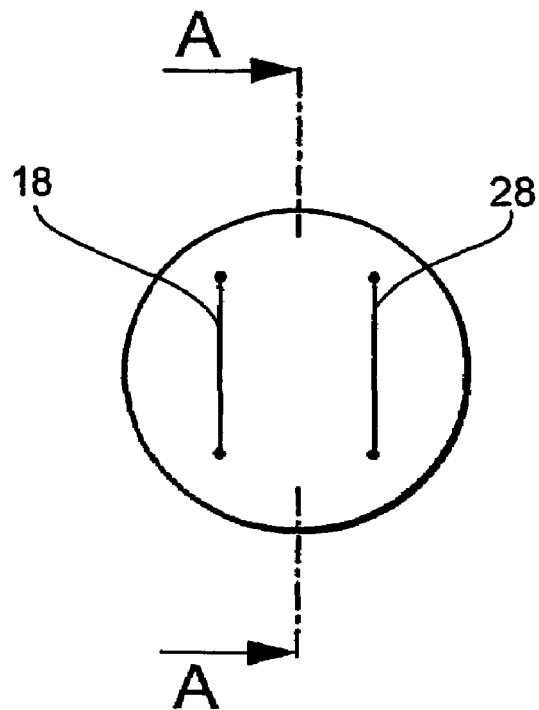
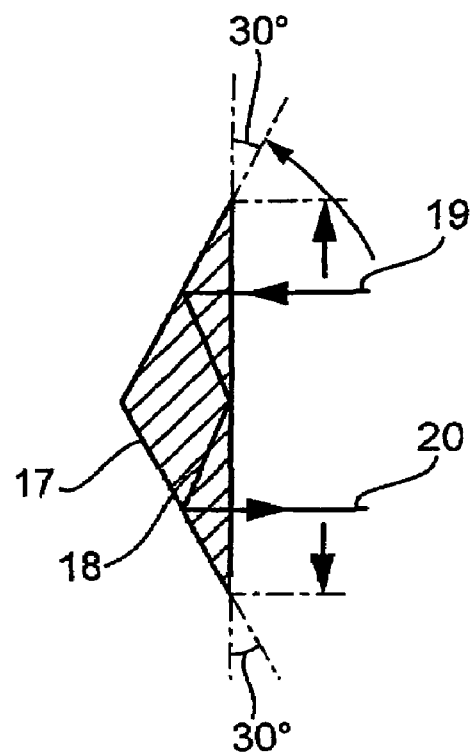
Fig. 3a
Fig. 3b
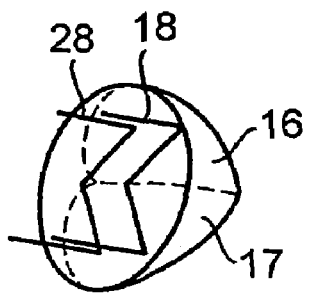
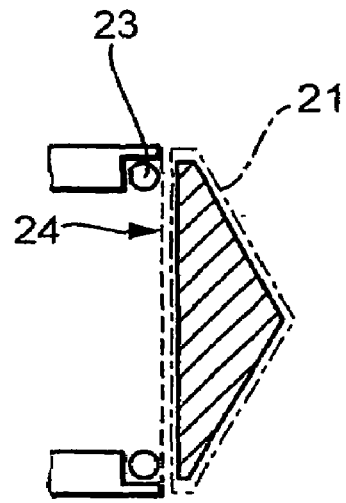
Fig. 3c
Fig. 3d

DEVICE FOR THE IR-SPECTROMETRIC ANALYSIS OF A SOLID, LIQUID OR GASEOUS MEDIUM

FIELD OF THE INVENTION

The invention relates to a device for IR-spectrometric analysis of a solid, liquid or gaseous medium by means of an optical probe. The probe can exhibit an ATR-, transmission- or reflection-structure.

BACKGROUND OF THE INVENTION

In ATR (attenuated total reflectance)-spectroscopy, the effect whereby a light beam at the interface between an optically more-dense medium of index of refraction $n_1$ and an optically less-dense medium of index of refraction $n_2$ is made use of. Thus, when: $n_1 > n_2$, and when the angle of incidence of the light beam exceeds the critical angle for total reflection, total reflection occurs. The sine of this critical angle corresponds to the quotient $n_2/n_1$. In the case of total reflection, the phenomenon occurs, in which the light beam exits at a contact point A into the less-dense medium, then moves as a surface wave past the more-dense medium as far as a point B, and finally turns back into the optically more-dense medium. If there is no absorption in the optically less-dense medium, then the light beam is totally reflected without any weakening. However, if the optically less-dense medium does absorb the penetrating radiation, then a weakening of the totally reflected light beam occurs. This weakening depends on the wavelength and can be used for so-called internal reflection spectroscopy. If one determines the transmission, or absorption, spectrum of the totally reflected radiation, then one obtains information concerning the composition of the optically less-dense medium. The optically less-dense medium can be, for example, an IR-absorbing, powdered substance, or a fluid medium, which the ATR-probe is directly contacting.

Currently, ATR-probes are preferably used for IR-spectroscopy or in the UV-VIS region. Essential element of an ATR-probe is a reflection element, which is made of a material of high index of refraction transparent in the IR-region. The known probes are embodied such that a plurality of reflections occurs within the reflection element.

U.S. Pat. No. 5,459,316 describes an ATR-probe for the IR-region that can be used in powdered or fluid media. Light is guided by way of a measuring tube to, respectively from, the ATR-crystal, with he lateral surface of the ATR-crystal facing the medium, and that facing away, are both wedge-shaped, as seen in cross section. Preferably, the embodiments of the ATR-crystal disclosed in this patent are rotationally symmetric about their longitudinal axis. The double-conical form of such an ATR-crystal, or of such an ATR reflection element, for the prevention of disturbing interferences in the Fourier transform (FT-IR) spectrometer is complicated and can be avoided by the use of the spectrometer proposed in this patent. Moreover, the reflection element proposed in U.S. Pat. No. 5,459,316 is too large in combination with an FT-I R spectrometer to be able to be produced cost-favorably from the ideal material diamond.

Additionally, the field of transmission spectroscopy has probes, in which the measurement section is defined by the separation of two optical windows. This leads to a probe body having relatively many components (windows, mirrors, holders). Analogously to the reflection element of an ATR-probe, a transmission arrangement is known, in which the reflection element has a slit. The measuring gap is defined by the width of this slit. As already mentioned, all known types of reflection elements can be used in connection with the present invention.

Concerning the radiation receiver, the field of gas measurement technology additionally has systems, in which the reflected and wavelength-dependently weakened light reaches a pixel-array detector via a special linear variable filter matched to the particular application. A corresponding application is described in U.S. Pat. No. 5,920,069. Subsequently, the intensity value measured in each detector element of the pixel array detector is evaluated for the purpose of producing the spectrum of the test sample.

A disadvantage of this embodiment, in which the measurement value detection occurs in parallel, is, firstly, the large number of pixel detectors. Additionally, only a fraction of the total intensity is measured in each of the pixel detectors, with this fraction being smaller, the greater the number of pixel detectors. Due to an unfavorable signal/noise ratio, one obtains a relatively poor signal resolution using this technique. Disadvantageous in this known embodiment is, moreover, that specially embodied pixel array detectors matched to the particular application lead to high manufacturing costs, and, despite the expenditure, usually one or more defective pixel detectors or even non-linear characteristic curves.

SUMMARY OF THE INVENTION

An object of the invention is to provide a cost-favorable device for the spectrometric analysis of a medium to be measured.

The object is achieved in a first variant of the invention by a device having a process probe with a reflection element, a linear variable filter, at least one detector element and a control/evaluation unit. Additionally belonging to the device of the invention are at least one light source, whose light is coupled either with or without optical waveguide into the reflection element via a collimator optics or an ellipsoidal mirror, and at least one optical waveguide with an input section and an output section. The light is guided via the output section of the waveguide into defined regions of the linear variable filter; the detector element and the linear variable filter are arranged movably relative to one another over approximately the length of the linear variable filter. The control/evaluation unit determines the spectrum of the medium on the basis of the measurement values delivered by the detector element.

The radiation can be coupled out of the reflection element via the input section of the waveguide loss-freely especially by means of a focusing unit. The waveguide, which is usually an optical waveguide bundle, guides the light weakened in the reflection element through the linear variable filter for the wavelength-selective detection. The detector element and the output section of the waveguide are positioned opposite one another and are both arranged movably relative to the linear variable filter over approximately the length of the linear variable filter, with the linear variable filter being located between the detector element and the output section of the waveguide.

According to an alternative variant of the invention, the relative movement, and thus the scanning of the spectrum of the medium being measured, occurs such that the radiation source and the linear variable filter are moved relative to one another. In this solution, thus already monochromatic radiation is coupled into the reflection element.

By the two combinations of the invention mentioned above, a very compact and cost-favorable spectrometer module can be manufactured. The optical waveguide is a hollow conductor or a light conducting fiber transparent in the IR-region. For instance, the fiber is made from silver halide. A fiber of this polycrystalline material distinguishes itself by being very flexible, vibrationally stable, with an easily formable cross section and a suitability for high temperatures. Of course, the optical waveguide can be embodied in the form of a fiber bundle, depending on application. The individual fibers of the bundle have either a round or a polygonal cross section, for instance a rectangular cross section. The arrangement of the individual fibers in the bundle is determined by the optimal fitting to the spectrometer.

In an advantageous further development of the device of the invention, the control/evaluation unit controls the relative movement between the detector element and the linear variable filter. Of course, the detector element, the output section of the optical waveguide and the linear variable filter can also be moved continuously past one another.

One embodiment of the device of the invention provides that the detector element is fixedly mounted and the control/evaluation unit moves the linear variable filter stepwise or continuously past the detector element. Alternatively, it is proposed that the linear variable filter is fixedly mounted and the control/evaluation unit moves the detector element stepwise or continuously past the linear variable filter.

In both variants, a preferred embodiment of the device of the invention is provided with a fork-shaped holding device, in which the detector element and the output section of the optical waveguide are mounted. For producing the proposed relative movement, either the holding device or the detector element or the linear variable filter are arranged on a guide rail. Considered especially advantageous in connection with the device of the invention is the use of a stepper motor for stepwise or continuous movement of the linear variable filter or the detector element, respectively the holding device for the detector element.

An advantageous further development of the device of the invention includes that the optical waveguide, which guides the measuring light from the reflection element to the linear variable filter, is a cross-section converter. In this way, a linear row of individual optical waveguides in the output section of the optical waveguide can achieve an increase of light throughput through the linear variable filter.

In addition, an embodiment of the device of the invention provides a second input section of the waveguide, via which the radiation, or the light, of the radiation/light source, is coupled-in as an internal reference beam, through a partially reflecting element. Especially, an alternating radiation source with one or two radiators is provided, via which, with the help of the detector, a sequential measuring of the measuring light and the reference light is enabled. For this purpose, the waveguide is provided in one embodiment in the form of an optical fiber duplexer having two input sections and one output section. Of course, the light can also be guided via some other optical system to the linear variable filter and subsequently to the detector element.

Preferably, the detector element is a single-element detector, possibly also a pixel-array detector. Advantageous is the use of pyroelectric detectors, since these eliminate any requirement for additional cooling and are cost-favorable in comparison to semiconductor detectors.

According to a favorable embodiment of the device of the invention, the reflection element is made of a highly pure semiconductor material. Preferred examples in this case are silicon or germanium, which are both transparent in the IR-region. According to the invention, the reflection element can be prepared very cost-favorably from a wafer of highly pure semiconductor material. For this purpose, cylinder-shaped disks are drilled out of a wafer. A cylinder-shaped disk has, for example, a thickness of 2 to 5 mm. Facets are ground on both sides of the cylinder-shaped disks, so that the reflection element has the form of a roof. The reflection element in the probe tube is then fitted into e.g. a retractable assembly, or into a process connection, for the process probe, so that the medium being measured cannot escape from the process in the case of removal of the probe. Known retractable assemblies usable in connection with the present invention are available from the assignee under the mark CLEANFIT (see also DE 19948990 A1). Of course, the wafer, or the reflection element, can, in principle, be made of any material transparent in the IR-region.

In an advantageous further development of the ATR-probe of the invention, or of the reflection element of the invention, at least the region of the reflection element that comes in contact with the medium to be measured is provided with a thin diamond layer. Preferably, the diamond layer is a monocrystalline coating. This diamond layer makes the reflection element itself inert against aggressive and corrosive media. In the case of suitable choice of the internal reflection angle of the basic body (which is made e.g. of a semiconductor material), the application of the diamond layer enables adjustment of an internal reflection angle; here, the ATR-effect can be utilized. A special geometry of the reflection element permits a highly compact embodiment, in which two product-contacting reflections occur in the coated reflection element on the basis of an intermediate reflection at the in/out coupling surface.

In order to exclude systematic measurement errors, besides the spectrometric examination of the measurement beam, an examination of a reference beam is performed in parallel. The reference beam takes a path through the ATR-probe which is analogous to that of the measuring beam; however, by appropriate coatings of the contact points in the reflection element, it is made certain in doing this, that no reference light can escape into the optically less-dense medium, i.e. into the medium actually being measured. The total reflection is achieved without the weakening effect, for example, by the partial application of a metal coating. Preferably, the contact points of the reference light on the side surface of the reflection element facing the medium to be measured are, therefore, provided with a vapor-deposited metal layer.

In order to avoid as much as possible an intensity loss in the measuring light, or the reference light, as the case may be, at the in/out coupling of the light in the reflection element, the surface of the reflection element facing away from the medium being measured preferably carries an anti-reflection layer.

According to an advantageous further development of the device of the invention, the reflection element is dimensioned and embodied such that the measuring light, or the reference light, as the case may be, experiences up to seven reflections in the reflection element. The actual number of reflections can, in this form of embodiment, be determined by the length of the reflection element. In this way, especially weak absorption bands of the medium being measured are detected better than is possible at a lower number of reflections. The wavelength of the measuring light, or the reference light, as the case may be, lies preferably in the wavelength region from 5 to 14 µm.

In a preferred embodiment, the reflection element is a microprism. Preferably, the microprism is made of diamond; however, other materials are also usable. The structure of an infrared micro-measuring probe is, as well, described in detail in DE 100 34 220 A1. The probes described in this publication are usable in connection with the present invention; however, in contrast to the disclosure of DE 100 34 220 A1, the use of conical mini-prisms is preferred and special value is placed on the arrangement of the optical waveguides in the bundle.

The forms of embodiment of the reflection elements according to the invention have the decisive advantage that the incoming and outgoing beams are parallel to one another, both in the case of the measuring light and in the case of the reference light. With corresponding, equal dimensioning of the different reflection elements (ATR and transmission) on the in-coupling and out-coupling side, the probe can be adapted for particular measurement tasks just by exchanging the reflection elements.

Of course, it is possible in the first form of embodiment of the device to place the at least one radiation, or light, source in the immediate vicinity of the reflection element, so that there is no need for an optical waveguide on the in-coupling side. Preferably, the radiation source is an electronically-pulsed light source without movable parts. Naturally, a mechanical chopper can also be used.

The invention will now be explained in greater detail on the basis of the drawings, the figures of which show as follows:

BRIEF DESCRIPTION OF THE DRAWINGS

FIG. 2a is a schematic presentation of a cross-section converter with optical fiber duplexer;

FIG. 2b is a front view of the input and output sections of the cross-section converter of FIG. 2a;

FIG. 3a is a front view of a first form of embodiment of the ATR reflection element of the invention;

FIG. 3b is a cross section of the form of embodiment shown in FIG. 3a taken on the cutting plane A-A of FIG. 3a;

FIG. 3c is a perspective view of the form of embodiment shown in FIG. 3a;

FIG. 3d is a schematic representation of a form of embodiment of the process seal of the ATR reflection element of the invention;

FIG. 4b is a side view of the form of embodiment shown in FIG. 4a, taken according to the reference A-A of FIG. 4a;

FIG. 4d is perspective views of the form of embodiment shown in FIG. 4a;

FIG. 5b is a side view of the form of embodiment shown in FIG. 5a, according to the reference A-A of FIG. 5a;

FIG. 5d is a perspective view of the form of embodiment shown in FIG. 5a;

DESCRIPTION OF THE PREFERRED EMBODIMENTS

Figure 1:
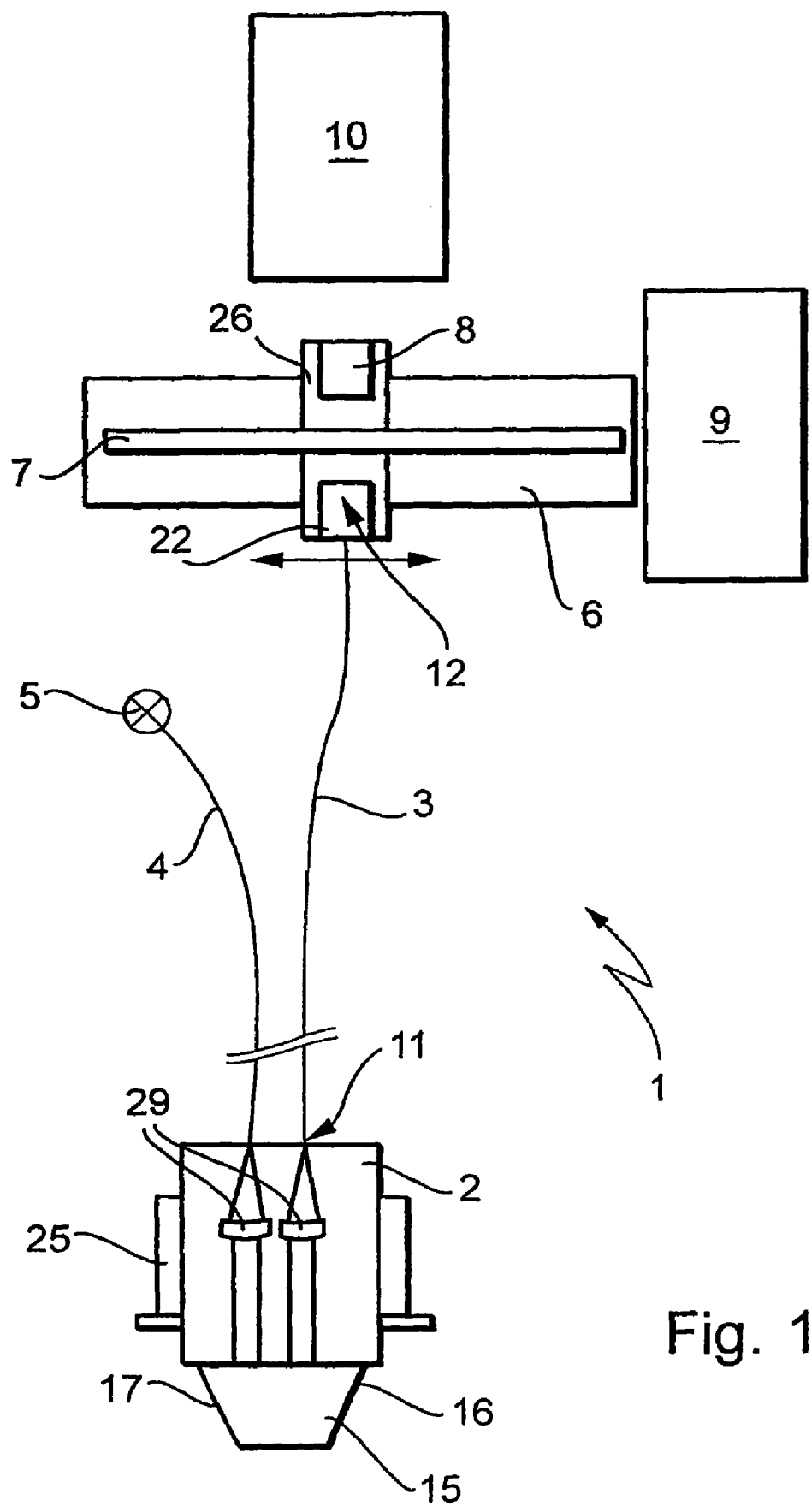
FIG. 1 is a schematic presentation of a first embodiment of the device of the invention.

FIG. 1 is a schematic drawing of a first embodiment of the device 1 of the invention.

FIG. 1 is a schematic drawing of a first embodiment of the device I of the invention. The ATR-probe 2 includes thee process assembly 25 and the reflection element 15. The process assembly 25 is, for example, a retractable assembly, such as that available from Endress + Hauser. under the mark CLEANFIT. An interesting aspect of the invention concerns different geometrics of the reflection element 15, as will be described in more detail below. Independent of the selected geometry, the reflection element 15 is mechanically protected by the process assembly 25, yet nevertheless comes into direct contact with the medium being measured.

Figures 2A, 2B:
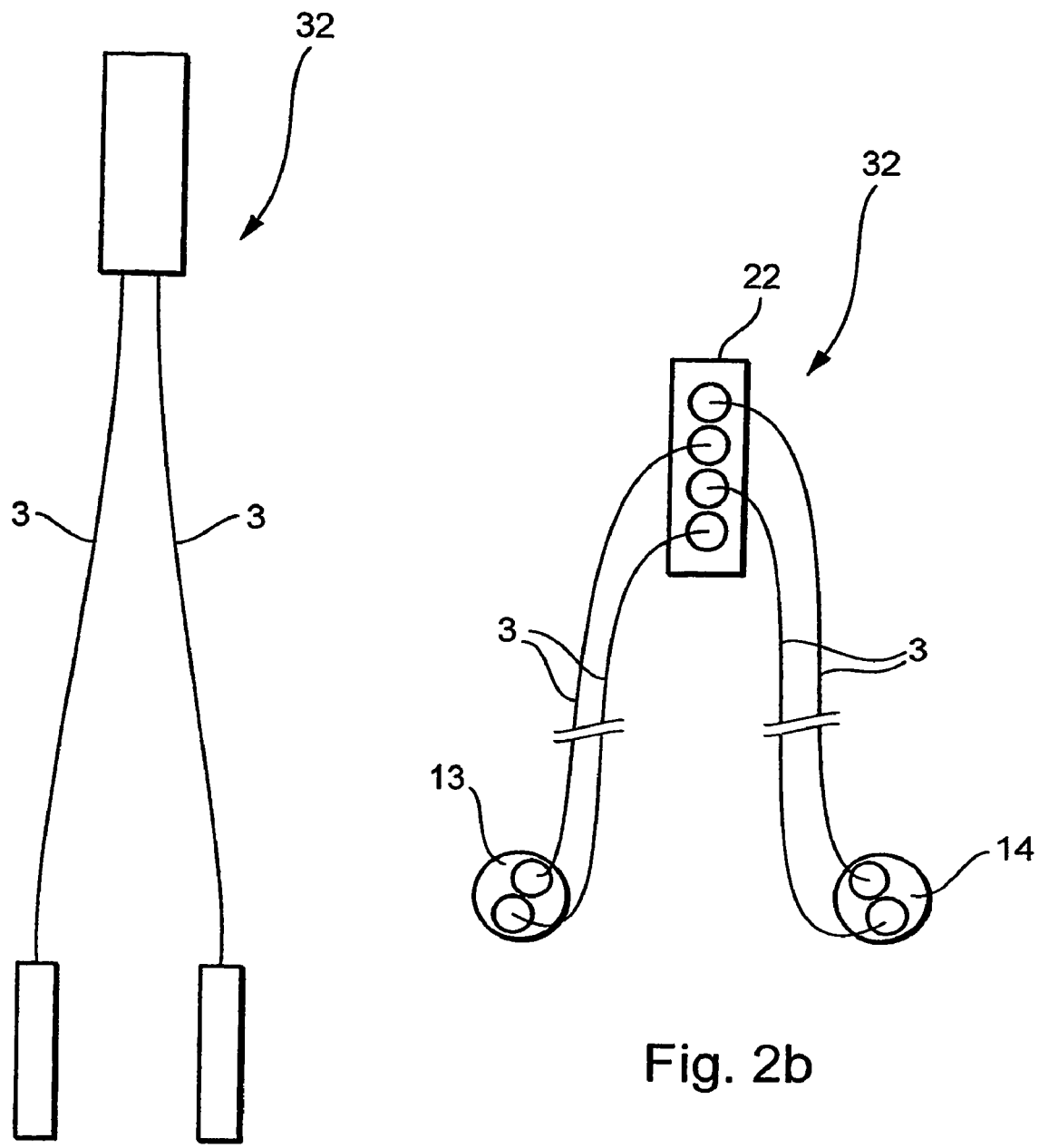
Figure 4A:
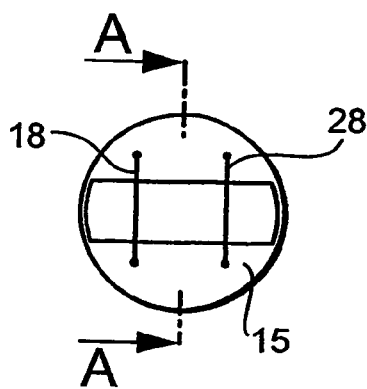
FIG. 4a is a front view of a second form of embodiment of the ATR reflection element of the invention.
Figure 4B:
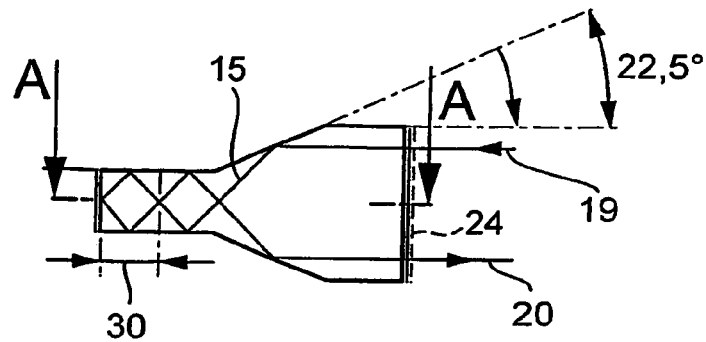
Figure 4C:
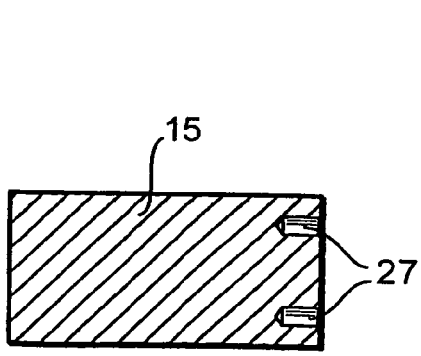
FIG. 4c is a cross section taken on the cutting plane A-A of FIG. 4b.
Figure 4D:
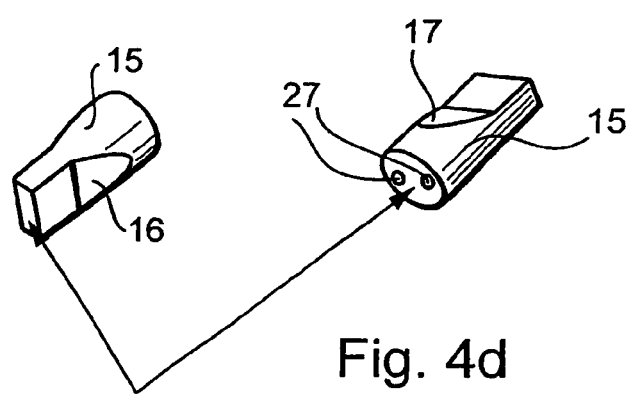
Figure 5A:
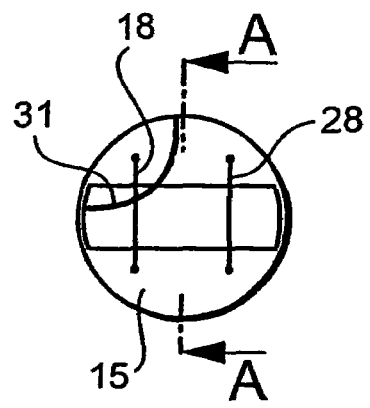
FIG. 5a is a front view of a third form of embodiment of the ATR reflection element of the invention.
Figure 5B:
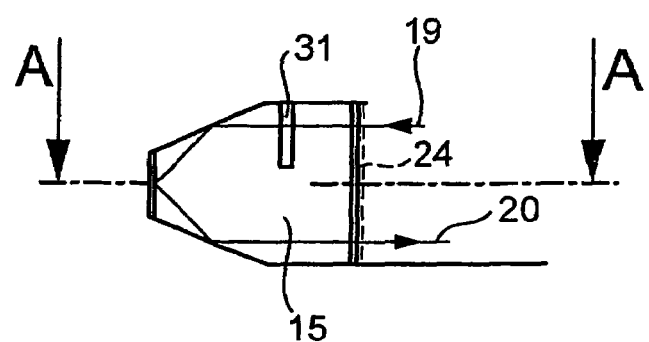
Figure 5C:
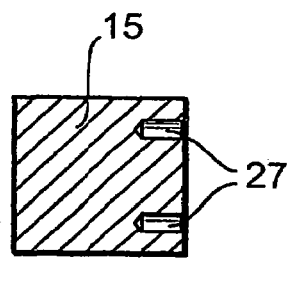
FIG. 5c is a cross section taken according to the cutting plane A-A of FIG. 5b.
Figure 5D:
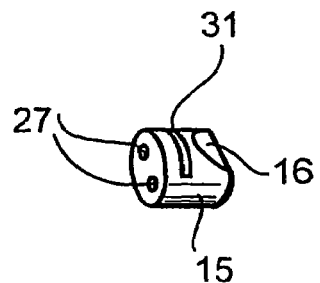

The measuring light and the reference light, which preferably originate in two light sources 5, are coupled into the ATR-probe 2 via the optical waveguide 4. Both the optical waveguide 4 and the optical waveguide 3 are preferably optical fiber bundles. Corresponding embodiments are presented in FIG. 2a (side view) and FIG. 2b (front view). Of course, other in-couplings are likewise possible. Also, light source 5 can be positioned directly in front of the reflection element 15, in which case the optical waveguide 4 can be omitted.

A cross-section converter 22 is located in the area of the light output section 12. The cross-section converter transitions the individual optical fibers for the measuring light and reference light into a plurality of mutually superimposed fibers. The measuring and reference lights pass through the linear variable filter 7 and their intensities are then registered by the detector element 8.

The cross-section converter 22 and the detector element 8 are secured on a holding device 26, which is arranged movably on a guide track 6. The holding device 26 is moved successively past the linear variable filter by drive 9. Linear variable filters are known; U.S. Pat. No. 5,920,069 is incorporated here by reference in this connection.

The drive 9 is, for example, a stepper motor, which moves the holding device 26 by way of a spindle not separately shown in FIG. 1. The detector element 8 measures the intensity values of measuring light and reference light in each position achieved by the holding device as it is driven by the stepper motor. On the basis of these values, the control/evaluation unit 10 produces the spectrum of the medium being measured, based on its contact with the reflection element 15. The spectral distribution provides information on which substance/substances is/are in the medium being measured, in which concentration. The evaluation proceeds on the basis of the known algorithms.

FIGS. 3, 4, 5 show different variants of the reflection element 15 of the invention for the ATR-probe 2. Of course, use of reflection element 15 is not limited to the device 1 of the invention described with respect to FIG. 1. Rather, the reflection element 15 in the process probe 2 can be connected to any spectrometer/spectrograph utilizing an optical waveguide coupling.

As already indicated, the reflection element 15 of the invention is made of a material which is highly transparent in the IR-region. Preferably, the material is a semiconductor material, e.g. highly pure silicon or germanium. For increasing the resistance of the semiconductor material to withstand aggressive or corrosive media to be measured, at least the areas coming in contact with the medium being measured are provided with a diamond coating 21. A form of embodiment adapted in this way is presented in FIG. 3d, which shows reflection element 15 in cross section.

The reflection elements 15, respectively the ATR-prisms, of the invention are preferably drilled as cylindrically shaped disks from a semiconductor wafer. Subsequently, facets 16, 17 are ground toward both sides of the cylindrically shaped disk, so that the reflection element 15 has the form of a ridged, or saddle, roof on the side facing the medium to be measured. The corresponding embodiment of the reflection element 15 is shown e.g. in FIGS. 3a, 3b and 3c.

These figures additionally show the ray path 18 of the measuring light. The collimated light bundle coming from the light source 5 is reflected in the area of facet 16 of the reflection element 15. At the boundary surface with the optically less-dense medium being measured, the measuring light experiences on contact with the medium being measured a first weakened total reflection; a second weakened total reflection occurs on the facet 17. The total reflection at the in-coupling, out-coupling surface of the reflection element 15 facing away from the medium being measured occurs approximately without weakening. This is a consequence of the angle of incidence, respectively angle of reflection, which in the illustrated example is approximately 60°. Additionally, the in-coupling/out-coupling surface can be provided with an anti-reflection coating 24.

The facets 16, 17 are ground such that the angle of incidence and the angle of reflection for total reflection in the case of perpendicular incidence of the measuring light onto the in-coupling/out-coupling surface amounts to about 30°. Additionally, for the illustrated case, the diameter of the reflection element 15 is dimensioned such that the measuring light experiences only three reflections within the reflection element. Because of the short travel distance of the measuring light within the reflection element 15 achieved in this way, the absorption losses in the material of the prism are kept small.

It is self-evident that every other form of facet grinding is possible, so long as the limit angle for total reflection is not subceeded, or fallen beneath. Embodiments of the reflection element 15 of the invention include that other weakened and unweakened total reflections of the measuring light, respectively reference light, can occur on the boundary surfaces of the reflection element. In any actual embodiment of the reflection element, one naturally designs toward, on the one hand, an optimizing of the light recovery and, on the other hand, an optimizing of measurement accuracy (number of reflections).

A major advantage of the various embodiments of the reflection element of the invention—as FIGS. 3, 4 and 5 make clear—is to be seen in the feature of having incoming and outgoing measuring light (respectively reference light) running parallel to one another. This simplifies the mechanical construction of the collimating optics 29.

The form of embodiment of the reflection element 15 shown in FIGS. 4 and 5 differs from that of FIG. 3 in that the ATR reflection element 15 of FIG. 4 displays a higher number of reflections at an internal reflection angle of 45°. The number of reflections can be increased by way of the lengthening distance 30 of the prism.

FIG. 5 shows a reflection element 15 having a lateral measuring slot 31. This form of embodiment thus is a transmission design. The two holes 27 in the in-coupling/out-coupling surface (FIGS. 4 and 5) are part of a not-separately shown, anti-twist securement, which fixes the reflection element 15 in the correct position relative to the collimating optics, following securement of the element 15 in the process probe 2. Anti-twist securement is achieved e.g. by insertion of appropriately formed pins into the holes 27. Of course, any other type of anti-twist securement can be used, so long as it does not disturb the ray paths 18, 28 of measuring light and reference light.

In FIGS. 3a, 3c, 4a and 5a, the ray path 28 of the reference light is drawn-in stylized alongside the ray path 18 of the measuring light. While the measuring light experiences a weakened total reflection in each of the regions of the facets 16, 17, the corresponding regions for the reference light are so embodied that the reference light does not experience a weakening at reflection on the facets 16, 17. To this end, the corresponding regions are provided, for instance, with a metal coating, which cannot be penetrated by IR-radiation.

Figure 6:
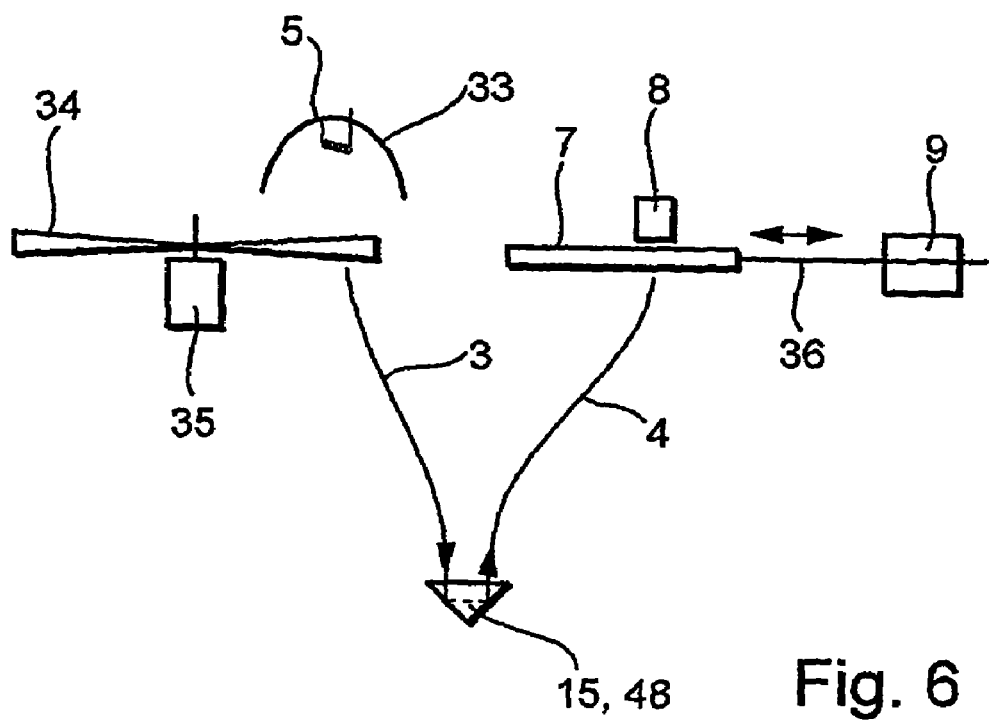
FIG. 6 is a schematic representation of a second embodiment of the device of the invention.

FIG. 6 is a schematic drawing of a second embodiment of the device of the invention. The radiation, respectively the light, of the radiation source, or light source, is focused by an ellipsoidal mirror 33 onto the light input section of the waveguide 3. For modulating the measuring light and the reflection light, a chopper 34 is used, which is turned by a chopper motor 35. The light is conducted to the reflection element 15 via the optical waveguide 3. The reflection element 15 is, in this case, a micro-prism 48 made from diamond. Preferably, the microprism 48 has the conical form shown in FIG. 6. Subsequently, the radiation, which has the information concerning the composition of the medium being measured, is conducted via the waveguide 4 in the direction of the linear variable filter 7 and the detector element 8. In the illustrated case, the detector 8 is fixedly mounted, while the linear variable filter is moved past the detector element 8 stepwise or quasi-continuously by the drive 9 and the spindle 36. In this way, the spectrum of the radiation is successively scanned. The evaluation of the spectrum occurs via the control/evaluation unit 10, which is not separately shown in FIG. 6.

Figure 7:
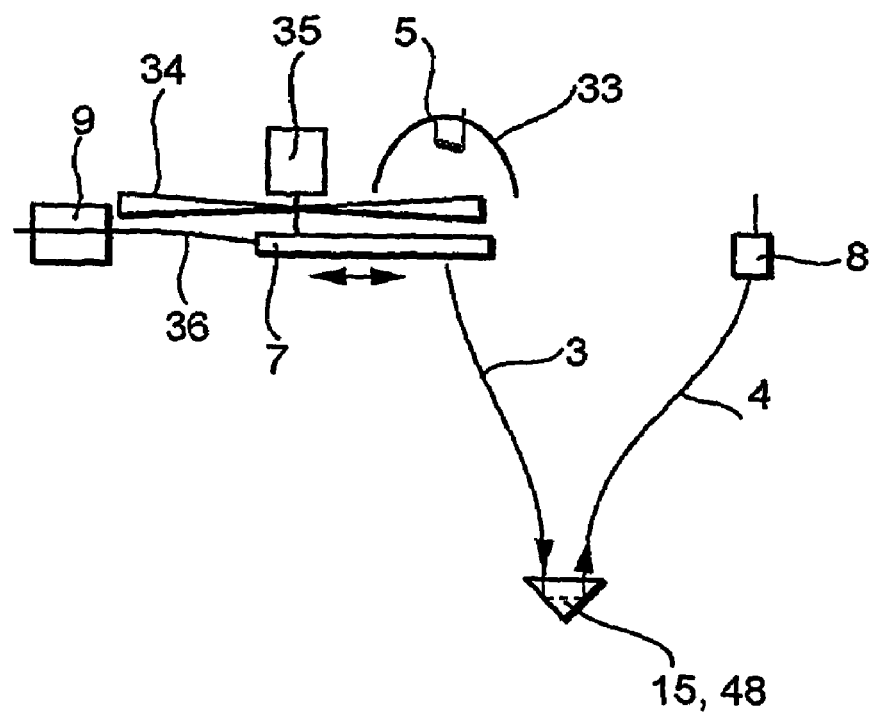
FIG. 7 is a schematic representation of a third embodiment of the device of the invention.

FIG. 7 sketches a preferred third embodiment of the device of the invention. This embodiment is distinguished, as in the embodiment of FIG. 6, by an especially simple and, consequently, cost-favorable construction. The light emitted from the light source 5 and pulsed by chopper 34 is focused by the ellipsoidal mirror 33 onto the input section of the waveguide 3. Between the radiation source 5 and the input section of the waveguide 3, the linear variable filter 7 is positioned. The linear variable filter is moved by the drive 9 and spindle 36 stepwise through the gap between the radiation source 5 and the input section of the waveguide 3, or the reflection element 15, as the case may be. After the radiation passes through the linear variable filter 7, the light is monochromatic. This monochromatic light is conducted to the reflection element 15 via the optical waveguide 3. The light reflected in the reflection element 15 is conducted into the detector element 8 via the optical waveguide 4.

Advantageous in this embodiment is that the optical waveguide 4 can be placed on the detector element 8 directly and, consequently, without losses. The coupling occurs preferably using the so-called pigtailing technique. This permits achievement of a higher light yield. As a result, the signal/noise ratio of the obtained spectra can be further increased, whereby the detection limit for substances in the medium being measured at the reflection element 15 is further reduced.

Figure 10:
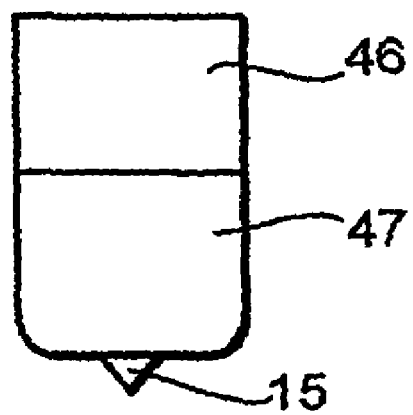
FIG. 10 is a schematic representation of the measuring tip of an ATR-probe having a microprism.

Preferably, the reflection element 15 of the embodiment shown in FIG. 7 is also an ATR-crystal. Preferably used as the ATR-crystal is a microprism 48 of diamond. FIG. 10 shows a prism of diamond secured on the tip of a process probe 2. The probe 2 is so embodied in the illustrated case that it takes into consideration the hygiene-requirements of the pharmaceuticals and food industries. In particular, the probe 2 has rounded edges. The probe tube 46 with the probe tip 47 is preferably made of titanium, Hastelloy or PEEK. The diamond, respectively the microprism 48, is, depending on the substance to be measured, soldered or adhered into the probe body. The probe 2 is so manufactured that it can be used in existing retractable assemblies, such as those available from the assignee.

Figure 8:
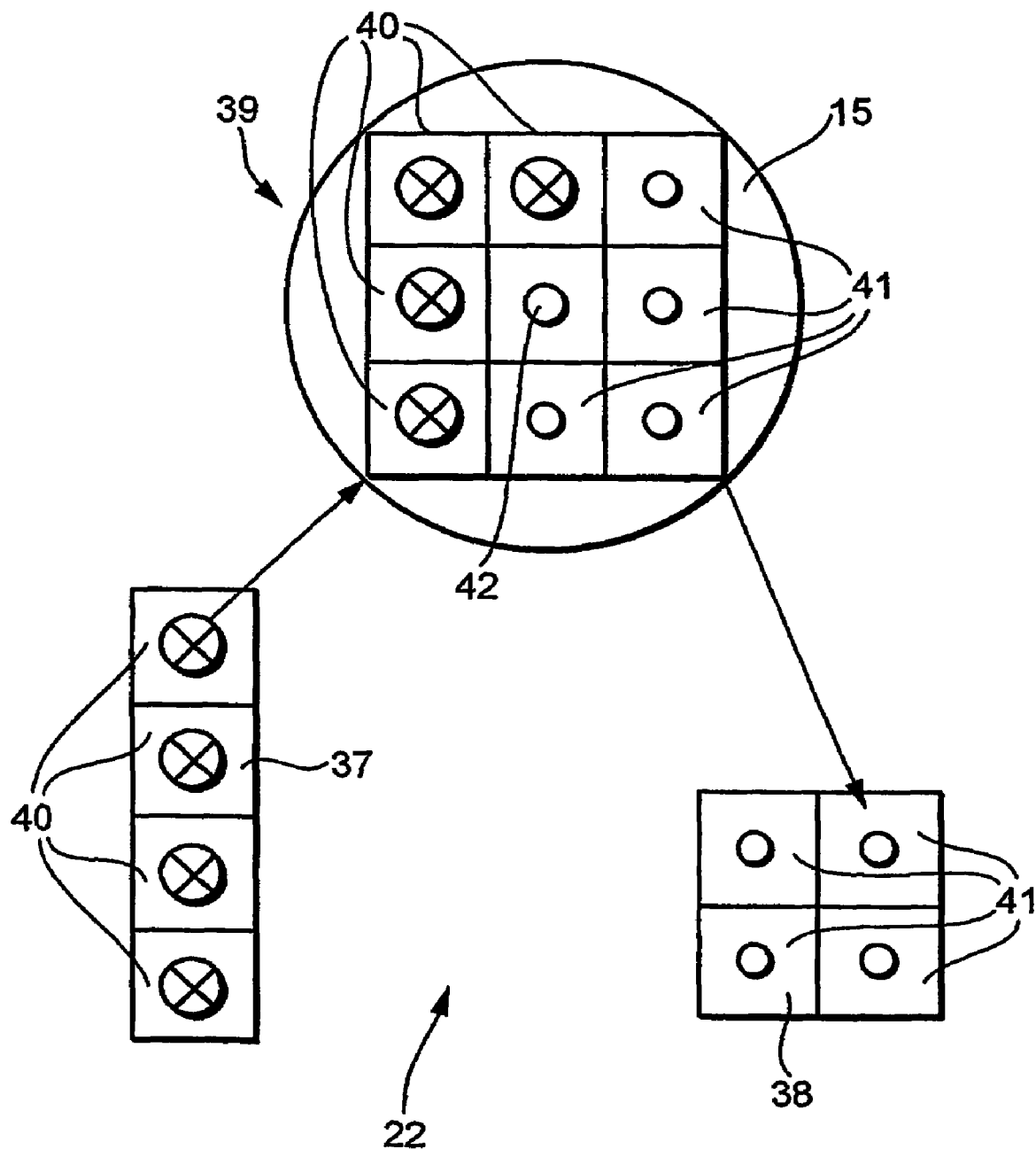
FIG. 8 is a schematic representation of a cross-section converter, which is preferably used with the embodiments of FIGS. 6 and 7.

FIG. 8 is a schematic presentation of a cross-section converter 22, which is preferably used in the embodiment of FIG. 7. The cross-section converter 22 is composed of three parts 37, 38, 39. The cross-section converter 37 is arranged in the direction of the linear variable filter 7 and has four fibers 40 arranged in a row. Fibers 40 conduct the monochromatic light in the direction toward the microprism 48. The cross-section converter 38, which is arranged in the direction of the detector element 8, likewise has four fibers 41, which are positioned in a quadratic shape. The cross-section converter 39, which is located directly in front of the circularly shaped end surface of the preferably cone-shaped microprism 48, has, for example, the design shown in FIG. 8. The fibers 40, 41 of the optical waveguides 3, 4 have, moreover, preferably the rectangular cross section shown in FIG. 8. Of course, the fibers 40, 41 of the invention can also be round.

Preferably, the reflection element 15 has, furthermore, the illustrated, conical shape. This has the advantage that the orientation of the quadratic cross-section converter 39 is rotationally invariant. Naturally, a quadratic or more-cornered, e.g. octagonal, base shape of the internal reflection element 48 is also possible; however, then the quadratic cross-section converter 39 must be aligned according to the base surface of the reflection element 48.

Figure 9:
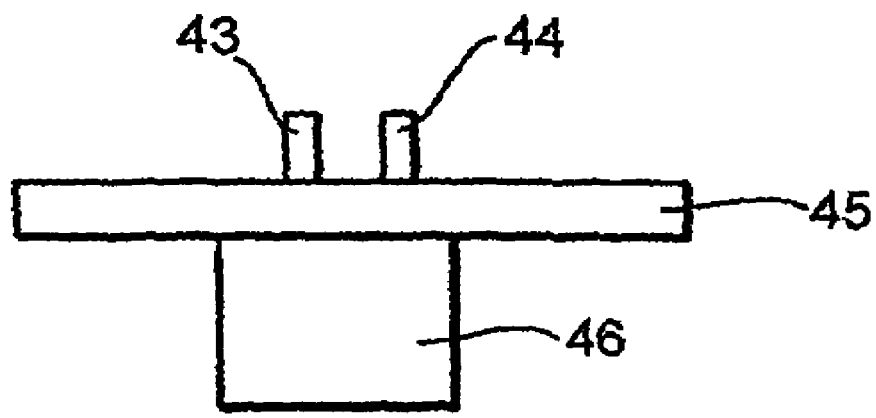
FIG. 9 is a schematic representation of a plug connector for mounting the optical waveguide to the LVF-spectrometer.

As shown in FIG. 9, the input section and the output section of the process probe 2 are integrated in a plug. Consequently, it is possible to connect the probe 2 easily with the linear variable filter 7. Preferably, the securement of the input, respectively output, section of the waveguides 3, 4 to the LVF-spectrometer is accomplished via ferrules 43, 44.

The invention claimed is:

1. A device for IR-spectrometric analysis of a solid, liquid or gaseous medium, comprising:
   a process probe, which has a reflection element which comprises a microprism;
   a linear variable filter,
   at least one detector element; and
   a control/evaluation unit, wherein:
   at least one radiation source is provided, whose electromagnetic radiation is coupled into said reflection element,
   at least one waveguide is provided, having an input section and an output section;
   said input section receives the electromagnetic radiation from said reflection element;
   the electromagnetic radiation is conducted via the output section of said waveguide into at least one defined area of said linear variable filter;
   said detector element receives the electromagnetic radiation from said linear variable filter;
   said detector element is arranged to be movable relative to said linear variable filter over essentially the length of said linear variable filter;
   and said control/evaluation unit determines the spectrum of the medium on the basis of the measured values delivered from said detector element.

2. A device for IR-spectrometric analysis of a solid, liquid or gaseous medium, comprising:
   a process probe, which has a reflection element which comprises a microprism;
   a linear variable filter;
   at least one detector element; and
   a control/evaluation unit, wherein:
   at least one radiation source is provided, whose electromagnetic radiation is focused into at least one defined region of said linear variable filter;
   at least one waveguide is provided, via which the electromagnetic radiation is coupled, after passing through said linear variable filter, into the reflection element,
   the focused electromagnetic radiation coming from said radiation source is arranged to be movable relative to said linear variable filter over essentially the length of said linear variable filter;
   said detector element receives the electromagnetic radiation after it has passed through said reflection element; and
   said control/evaluation unit determines the spectrum of the medium on the basis of the measurement values delivered from said detector element.

3. The device as claimed in claim 1, wherein:
said control/evaluation unit controls the relative movement between said detector element and said linear variable filter, stepwise or continuously.

4. The device as claimed in claim 1, wherein:
said detector element is mounted fixedly;
said radiation source is mounted fixedly; and
said control/evaluation unit moves said linear variable filter stepwise or continuously past said detector element.

5. The device as claimed in claim 1, wherein:
said linear variable filter is mounted fixedly;
said linear variable filter is fixedly mounted; and
said control/evaluation unit moves the detector element stepwise or continuously past said linear variable filter.

6. The device as claimed in claim 1, further comprising:
a holding device, in which said detector element and said output section, are mounted.

7. The device as claimed in claim 6, further comprising:
guide rail, wherein:
said holding device, said detector element, said radiation source or said linear variable filter are arranged on said guide rail.

8. The device as claimed in claim 1, wherein:
said output section and/or said input section includes a cross-section converter.

9. The device as claimed in claim 6, further comprising:
a drive wherein:
said drive is provided for moving said linear variable filter or said detector element, said radiation source, and said holding device for said detector element, and said radiation source, stepwise or continuously.

10. The device as claimed in claim 1, wherein:
said at least one waveguide is an optical fiber duplexer, via which the measuring radiation and a reference radiation are guided to said reflection element; and
the measuring beam and the reference beam are conducted to said linear variable filter.

11. The device as claimed in claim 1, wherein:
said detector element comprises a pyroelectric detector, which comprises one of: a thermopile, an MCT detector, and a detector array.

12. The device as claimed in claim 1, wherein:
said reflection element is manufactured from a high-purity semiconductor material.

13. The device as claimed in claim 1, wherein:
said reflection element is manufactured from a high-purity semiconductor material or another IR-transmittive material, to both of which a thin diamond coating is applied.

14. The device as claimed in claim 1, wherein:
said reflection element is so dimensioned and embodied that the ray path of said measuring light undergoes a plurality of reflections in said reflection element; and
the number of reflections is determinable via the length of said element.

15. The device as claimed in claim 1, wherein:
said reflection element has one of: a round, quadratic and polygonal cross sectional area.

16. The device as claimed in claim 15, wherein:
said first wave guide comprises a plurality of fibers and has on the side of said linear variable filter a linear fiber cross-section converter and on the side of said reflection element an L-shaped cross-section converter; and
said second wave guide comprises a plurality of fibers and has on the side of said reflection element an L-shaped fiber cross-section converter and on the side of said detector a quadratic fiber cross-section converter.

17. The device as claimed in claim 16, wherein:
the two fiber cross-section converters are integrated on the side of said reflection element into at least one holder, and are arranged in the immediate vicinity of the cross-sectional area of said reflection element on the cross-sectional area of said reflection element.

18. The device as claimed in claim 1, wherein:
said process probe comprises one of: an ATR probe, a reflection probe and a transmission probe.

* * * * *